(12) United States Patent
Elmasry et al.

(10) Patent No.: US 12,376,973 B2
(45) Date of Patent: Aug. 5, 2025

(54) SYSTEM AND METHOD FOR QUANTIFYING GAP ASSESSMENT EXAMINATION

(71) Applicant: New York Society for the Relief of the Ruptured and Crippled, maintaining the Hospital for Special Surgery, New York, NY (US)

(72) Inventors: Shady Elmasry, New York, NY (US); Carl Imhauser, New York, NY (US); Peter Sculco, New York, NY (US); Geoffrey Westrich, New York, NY (US); Cynthia Kahlenberg, New York, NY (US)

(73) Assignee: NEW YORK SOCIETY FOR THE RELIEF OF THE RUPTURED AND CRIPPLED, MAINTAINING THE HOSPITAL FOR SPECIAL SURGERY, New York, NY (US)

(*) Notice: Subject to any disclaimer, the term of this patent is extended or adjusted under 35 U.S.C. 154(b) by 559 days.

(21) Appl. No.: 17/797,564

(22) PCT Filed: Feb. 5, 2021

(86) PCT No.: PCT/US2021/016893
§ 371 (c)(1),
(2) Date: Aug. 4, 2022

(87) PCT Pub. No.: WO2021/158972
PCT Pub. Date: Aug. 12, 2021

(65) Prior Publication Data
US 2023/0074652 A1 Mar. 9, 2023

Related U.S. Application Data

(60) Provisional application No. 62/971,454, filed on Feb. 7, 2020.

(51) Int. Cl.
*A61B 5/00* (2006.01)
*A61F 2/46* (2006.01)
*A61B 90/00* (2016.01)

(52) U.S. Cl.
CPC ...... *A61F 2/468* (2013.01); *A61B 2090/3916* (2016.02); *A61F 2002/4633* (2013.01);
(Continued)

(58) Field of Classification Search
CPC .............. A61F 2/468; A61F 2002/4633; A61F 2002/4666; A61F 2002/4667;
(Continued)

(56) References Cited

U.S. PATENT DOCUMENTS 5,733,292 A * 3/1998 Gustilo ................ A61B 17/025
606/88
7,097,662 B2 8/2006 Evans, III et al.
(Continued)

OTHER PUBLICATIONS

Stephen Kurtz et al., "Prevalence of Primary and Revision Total Hip and Knee Arthroplasty in the United States From 1990 Through 2002", The Journal of Bone & Joint Surgery, Jul. 2005, pp. 1487-1497.
(Continued)

*Primary Examiner* — May A Abouelela
(74) *Attorney, Agent, or Firm* — Leason Ellis LLP

(57) ABSTRACT

Measured forces applied by a medical professional during a gap assessment can be measured. A plurality of force sensors is placed at a lateral ankle position, a medial ankle position, a lateral foot position, and/or a medial foot position, and each detects an applied force during an abduction-adduction examination. Further, a computing device receives, from each of the plurality of sensors during the abduction-adduction examination, data representing an applied force occurring during the abduction-adduction examination at respective ones of the lateral ankle position, the medial ankle
(Continued)

position, the lateral foot position, and the medial foot position. The computing device calculates, using the received data, respective peak applied forces during the abduction-adduction examination in extension and flexion, and provides information representing a correlation of the respective peak applied forces with other information.

19 Claims, 8 Drawing Sheets

(52) U.S. Cl.
CPC ............... *A61F 2002/4666* (2013.01); *A61F 2002/4667* (2013.01); *A61F 2002/4668* (2013.01)

(58) Field of Classification Search
CPC ........... A61F 2002/4668; A61F 2/4657; A61B 2090/3916
See application file for complete search history.

(56) References Cited

U.S. PATENT DOCUMENTS

| | | | | |
|---|---|---|---|---|
| 8,211,041 | B2* | 7/2012 | Fisher | A61B 17/88 600/595 |
| 9,095,275 | B2 | 8/2015 | Clark | |
| 9,585,615 | B2 | 3/2017 | Singh et al. | |
| 10,172,723 | B2 | 1/2019 | Fisher et al. | |
| 10,555,822 | B2 | 2/2020 | Fisher et al. | |
| 2010/0249658 | A1* | 9/2010 | Sherman | A61B 5/4528 606/53 |
| 2010/0249777 | A1* | 9/2010 | Sherman | A61B 5/1107 606/53 |
| 2014/0094715 | A1* | 4/2014 | Stein | G01L 11/02 600/587 |
| 2015/0238691 | A1* | 8/2015 | Boyden | A61B 5/11 604/66 |
| 2016/0029952 | A1* | 2/2016 | Hunter | A61F 2/34 600/595 |
| 2016/0100905 | A1* | 4/2016 | Maher | A61B 90/60 606/102 |
| 2016/0278944 | A1* | 9/2016 | D'Lima | A61F 2/4657 |
| 2017/0196704 | A1* | 7/2017 | Behzadi | A61F 2/4609 |
| 2017/0312099 | A1* | 11/2017 | Paszicsnyek | A61F 2/38 |
| 2018/0021151 | A1* | 1/2018 | Mantovani | A61F 2/4657 606/88 |
| 2018/0160977 | A1* | 6/2018 | Meere | A61B 5/224 |
| 2019/0076273 | A1* | 3/2019 | Goodchild | A61B 5/6878 |
| 2019/0167447 | A1* | 6/2019 | Angibaud | A61F 2/389 |
| 2019/0231252 | A1* | 8/2019 | Paszicsnyek | A61B 17/1764 |
| 2019/0290451 | A1* | 9/2019 | Trabish | A61B 5/4585 |
| 2019/0290452 | A1* | 9/2019 | Trabish | A61B 5/4585 |
| 2020/0000400 | A1* | 1/2020 | McKinnon | A61B 5/4585 |
| 2020/0069280 | A1* | 3/2020 | Behzadi | A61F 2/28 |
| 2020/0107945 | A1* | 4/2020 | Trousdale | A61B 5/1122 |

OTHER PUBLICATIONS

Leo A. Whiteside, MD et al., "Functional Medial Ligament Balancing in Total Knee Arthroplasty", Clinical Orthopaedics and Related Research, Nov. 2000, pp. 45-57.
John Bottros, MD. "Gap Balancing in Total Knee Arthroplasty", The Journal of Arthroplasty, Jun. 2006, pp. 11-15.
Thomas K. Fehring, MD, "Early Failures in Total Knee Arthroplasty", Clinical Orthopaedics and Related Research, Nov. 2001, pp. 315-318.
Sina Babazadeh et al., "The relevance of ligament balancing in total knee arthroplasty: how important is it? A systematic review of the literature", Orthopedic Reviews, Oct. 2009 (9 pages).
Darryl D. D'Lima, MD et al., "Dynamic Intraoperative Ligament Balancing for Total Knee Arthroplasty", Clinical Orthopaedics and Related Research, Jul. 2007, pp. 208-212.
Brian K. Daines, MD et al., Gap Balancing vs. Measured Resection Technique in Total Knee Arthroplasty, Clinics in Orthopaedic Surgery, Mar. 2014, pp. 1-8.
Douglas A. Dennis MD et al., "Gap Balancing versus Measured Resection Technique for Total Knee Arthroplasty", Clinical Orthopaedics and Related Research, Jan. 2010, pp. 102-107.
Jan Victor, MD et al., "How Isometric Are the Medial Patellofemoral, Superficial Medial Collateral, and Lateral Collateral Ligaments of the Knee?", The American Journal of Sports Medicine, Oct. 2009, pp. 2028-2036.
Mohammad Kia PhD et al., "Femoral Component External Rotation Affects Knee Biomechanics: A Computational Model of Posterior-stabilized TKA", Clinical Orthopaedics and Related Research, Jan. 2018, pp. 113-123.
Mohammad Kia et al., "A Multibody Knee Model Corroborates Subject-Specific Experimental Measurements of Low Ligament Forces and Kinematic Coupling During Passive Flexion", Journal of Biomechanical Engineering, May 2016 (12 pages).
International Search Report and Written Opinion in PCT Application No. PCT/US2021/016893, mailed May 5, 2021 (11 pages).

* cited by examiner

SYSTEM AND METHOD FOR QUANTIFYING GAP ASSESSMENT EXAMINATION

CROSS-REFERENCE TO RELATED APPLICATIONS

This application is a U.S. National Phase Application under 35 U.S.C. § 371 of International Patent Application No. PCT/US2021/016893, filed on Feb. 5, 2021 and entitled SYSTEM AND METHOD FOR QUANTIFYING GAP ASSESSMENT EXAMINATION, which is based on and claims priority to U.S. Provisional Patent Application No. 62/971,454, filed Feb. 7, 2020 and entitled SYSTEM AND METHOD FOR QUANTIFYING GAP ASSESSMENT EXAM IN TOTAL KNEE ARTHROPLASTY, all of which are incorporated by reference, as if expressly set forth in their respective entireties herein.

GOVERNMENT SUPPORT

This invention was made with government support under TL1TR002386 awarded by the National Center for Advancing Translational Sciences of the NIH. The government has certain rights in the invention.

FIELD

The present disclosure relates, generally, to data management and communications and, more particularly, to a system and method for standardizing and improving patient assessment and treatment.

BACKGROUND

Joint replacement is a common form of surgery and enables many individuals to function normally in ways that would otherwise not be possible. Typically, an artificial joint includes metallic, ceramic and/or plastic components that are fixed to existing bone. One of the more common joints that undergoes replacement surgery is the knee.

The structure of the human knee joint is very detailed in nature and essentially includes four bones. The lower extremity of the femur, or distal femur, attaches by ligaments and a capsule to the proximal tibia. The distal femur contains two rounded oblong eminences, the condyles, separated by an intercondylar notch. The tibia and the femur do not interlock but instead meet at their ends. The femoral condyles rest on the condyles of the proximal tibia. The fibula attaches just below and is parallel to the tibia, and the patella (knee cap) is at the front of the knee, protecting the joint and providing extra leverage. Cartilage lines the surfaces of the knee bones, cushions them, and minimizes friction and a pair of menisci lie between the femur and the tibia and serve as pockets for the condyles, and serve to stabilize the knee. Knee ligaments connect the knee bones and cover and stabilize the joint. The knee ligaments include the patellar ligament, the medial and lateral collateral ligaments, and the anterior (ACL) and posterior (PCL) cruciate ligaments.

A healthy knee allows the leg to move freely within its range of motion while supporting the upper body and absorbing the impact of the weight of the body during motion. The knee has generally six degrees of motion during dynamic activities: three rotations (flexion/extension angulations, axial rotation along the long axis of a large tubular bone, also referred to as interior/exterior rotation, and abduction-adduction angulations); and three translations (anterior/posterior, medial/lateral, and superior/inferior).

Total knee arthroplasty (TKA) is a well-known surgical procedure by which a diseased and/or damaged natural knee joint is replaced with a prosthetic knee joint. A typical knee prosthesis can include a femoral component, a patella component, a tibial tray or plateau and a tibial bearing insert coupled to the tibial tray. The femoral component generally includes a pair of laterally spaced apart condylar portions that have distal surfaces that articulate with complementary condylar elements formed in a tibial bearing insert.

An important part of total knee arthroplasty surgery involves surgical planning and preparation of the bones. Planning and preparation is important to ensure that prosthetic components and the bone surfaces are mated in a proper and optimized way, in which the surgeon determines the position of the bone cuts. Different kinds of measuring and indexing devices are known that assist surgeons to determine the location of a cut. Additionally, guide devices are available for a surgeon to guide a saw to cut bone. For example, guides, jigs, blocks and templates are available to guide a saw blade to accurately resect the bones.

After determining a desired position of a cut, a surgeon usually attaches a guiding device to the bone using suitable fastening mechanisms, including, but not limited to, pins and screws. Attachment to structures already stabilized relative to the bone, such as intramedullary rods, can also be employed. After stabilizing the guiding device at the bone, the surgeon uses the guiding component of the device to direct the saw blade in the plane of the cut. After preparation of the bones, the knee is typically tested with trial components and then the prosthetic components are selected.

In total knee arthroplasty (TKA), surgeons typically apply intraoperative gap assessment, also referred to as gap balancing, to inspect knee balance and soft tissue tensioning after implant trials are placed. Gap assessment is a principal way for surgeons to determine an appropriate tibial insert size, as well to determine whether to release ligaments or modify one or more bone cuts in order to achieve proper soft tissue tension. Such surgical decisions can have a significant impact on knee stability following TKA. In a typical case, a surgeon performs gap assessment by holding the foot and applying abduction and adduction forces to generate abduction and adduction torques at the knee level, while visualizing the medial and lateral gaps at different flexion angles. Unfortunately, this type of examination remains a feel-based, qualitative "art" that relies on the intuition, knowledge, and preferences of each individual surgeon.

Although tools are available to quantify gap assessment, such tools have various limitations, such as by focusing only on resulting medial and lateral gaps. The present system and method address these and other deficiencies in the art.

SUMMARY

A system and method are disclosed for assessing measured forces that are applied by a medical professional during a gap assessment examination associated with an arthroplasty procedure for a patient. In one or more implementations, a plurality of force sensors are provided, each one of the plurality of force sensors respectively placed at i) a lateral ankle position and a medial ankle position, ii) a lateral foot position and a medial foot position, or iii) a lateral ankle position and a medial ankle position and a lateral foot position and a medial foot position. Each of the plurality of force sensors is configured to detect an applied force at i) the lateral ankle position and the medial ankle position, ii) the lateral foot position and the medial foot position, or iii) the lateral ankle position and the medial ankle position and the lateral foot position and the medial foot position, respectively, during an abduction-adduction (also referred to in the art, generally, as varus-valgus) examination. Further, a computing device is provided having at least one processor, a memory, and an output, and that is configured by executing instructions. The computing device is configured to receive, from each of the plurality of sensors during the abduction-adduction examination, data representing an applied force occurring during the abduction-adduction examination at each respective ones of i) the lateral ankle position and the medial ankle position, ii) the lateral foot position and the medial foot position, or iii) the lateral ankle position and the medial ankle position and the lateral foot position and the medial foot position. Further the computing device is configured to calculate, using the received data, respective peak applied forces during the abduction-adduction examination in extension and flexion. Further, the computing device is configured to provide, via the output, information representing a correlation of the respective peak applied forces with information associated with at least one of: at least one previous gap assessment examination for the patient by the medical professional; at least one previous gap assessment examination for a different patient by the medical professional; and at least one previous gap assessment examination for at least one different patient by at least one different medical professional.

In one or more implementations, medial and lateral gaps are determined at different flexion and extension angles during the gap assessment examination exam.

In one or more implementations, the information representing the correlation is in accordance with the determined medial and lateral gaps, and further wherein the information representing the correlation includes at least one of an accurate gap assessment examination and information associated with at least one surgical procedure.

In one or more implementations, the information associated with at least one surgical procedure includes a recommended insert size, a recommendation for a bone cut to achieve a threshold of soft tissue tension, or a degree to release ligaments.

In one or more implementations, bone or joint movement is tracked, as a function of at least one marker, during the gap assessment examination, and an adduction angle or degree of rotation is measured, as a function of the movement.

In one or more implementations, a 3-D model is generated and provided, via the output, that demonstrates a gap based on the measured adduction angle.

In one or more implementations, the output comprises a display, and further wherein the information representing the correlation is formatted as a graph.

In one or more implementation, each of the plurality of sensors comprises an elongated sensor that is configured to measure a total force, and further comprises internal electronics and a communications module to permit wireless transmission of data to a remote computing device.

In one or more implementations, applied force measurements are recorded from each of the plurality of sensors, during an abduction examination in flexion, during an abduction examination in extension, during an adduction examination in flexion, and during an adduction examination in extension, and wherein the information representing the correlation is in accordance with each of the recorded applied force measurements.

It is with respect to these and other considerations that the disclosure made herein is presented.

BRIEF DESCRIPTION OF THE DRAWINGS

Aspects of the present disclosure will be more readily appreciated upon review of the detailed description of its various embodiments, described below, when taken in conjunction with the accompanying drawings, of which.

DETAILED DESCRIPTION OF CERTAIN IMPLEMENTATIONS

By way of introduction and overview, the present disclosure provides an alternative system and method for gap assessment examination and surgical assistance in arthroplasty procedures. In one or more implementations, a system and method are provided to quantify forces/torques that are applied during intraoperative gap assessment for total knee arthroplasty (TKA). One of ordinary skill will recognize that additional kinds of arthroplasty are envisioned and supported in accordance with the teachings herein. In one or more implementations of the present disclosure, gap assessment examinations are standardized and usable to ensure optimal selections of inserts and procedures associated therewith. Further, the present disclosure is usable to provide recommendations and/or suggestions prior to, during, or after surgical procedures. Further, in one or more implementations, the teachings herein can be used as part of a training program for medical residents and fellows to develop skills regarding intraoperative examination.

As described herein, a system and method for gap assessment examination in total knee arthroplasty is provided and, in particular, a system comprising at least one tool is configured to quantify force/torques applied by surgeons during gap assessment. In other words, the present system and method can quantify clinical examination information in total knee arthroplasty to determine and identify the magnitude of forces applied by surgeons during the abduction-adduction exam. In one implementation, a surgeon or clinician receives information associated with magnitudes of forces and quantified data associated therewith.

Figure 1:
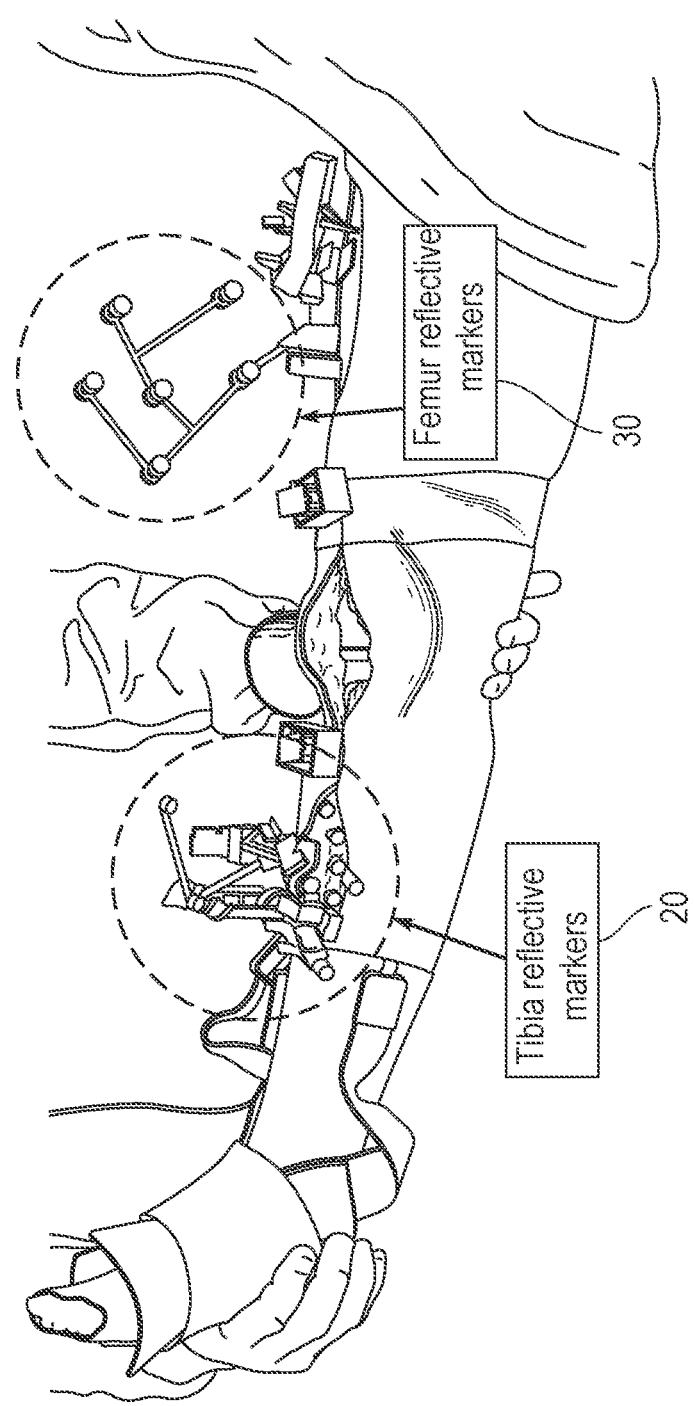
FIG. 1 shows an example knee that is undergoing a TKA procedure.

Referring now to the drawings, in which like reference numerals refer generally to like elements, FIG. 1 shows a knee that is undergoing a TKA procedure. As is known and shown in FIG. 1, motion capture technology can be utilized during a surgical procedure. Motion capture refers, generally, to the process of recording the movement of objects or people. Motion capture has widespread use and is used in various applications, for example, in military, entertainment, sports, and medical applications. In accordance with the present disclosure, motion capture is part marking and tracking the body, and part converting information associated with marking and tracking into useful data, including for clinical and research purposes. The amount, detail, and precision of motion capture information to provide to a user can depend on how the data are collected, in view of respective abilities and constraints with both accuracy and flexibility of accessing and providing the information in accordance with various implementations.

One common motion capture technique involves use of marker or optical systems. In such instances, motion capture can be achieved using infrared cameras and reflective markers. Generally, motion capture occurs from recording motion from cameras and tagged body parts, or estimates of motion by using more limited cameras and sensors. After the data are captured, additional filtering and calculations can be performed, such as to normalize and format the data, including to ensure that motion artifacts do not create false reporting. In such instances, reflective markers are placed on the body with specific guidelines to ensure the data gathering is accurate and precise, as muscle and skin can move at high velocity which creates a challenge with data quality. Anatomical landmarks can be selected for based on respective reliability and values in connecting joint motion. The data can be converted and for animations, simulations, reporting, and/or recommendations made during procedures. The respective results can be saved for future use and viewing, including to confirm the accuracy or correctness of various selections and decisions made during arthroplasty.

Continuing with FIG. 1, an implementation of motion capture technology is represented in a first set of reflective markers 20 and a second set of reflective markers 30. In the example shown in FIG. 1, the first set of reflective markers 20 is fixedly attached to tibia and the second set of reflective markers 30 is fixedly attached to the femur. Conventional anchoring hardware is used to attach the reflective markers to the respective anatomical landmark (bone). While the illustrated motion capture technology incorporates reflective markers, it is to be appreciated that other motion capture technologies can be used.

In accordance with the present disclosure, motion capture technology can be used to track bone and joint movement and more particularly, to measure an adduction angle. As used herein, adduction represents movement of a body part toward the body's midline. In contrast, abduction is any motion of the limbs or other body parts that pulls away from the midline of the body. In TKA, two vectors can used to calculate the angles of abduction and adduction, with these two vectors being perpendicular to the hypothetical anatomical axis of the femur and connect the lateral femoral condyle with the medial femoral condyle. It is a vector perpendicular to the imaginary anatomical axis and connects the tibial lateral and the tibial medial.

Figure 2:
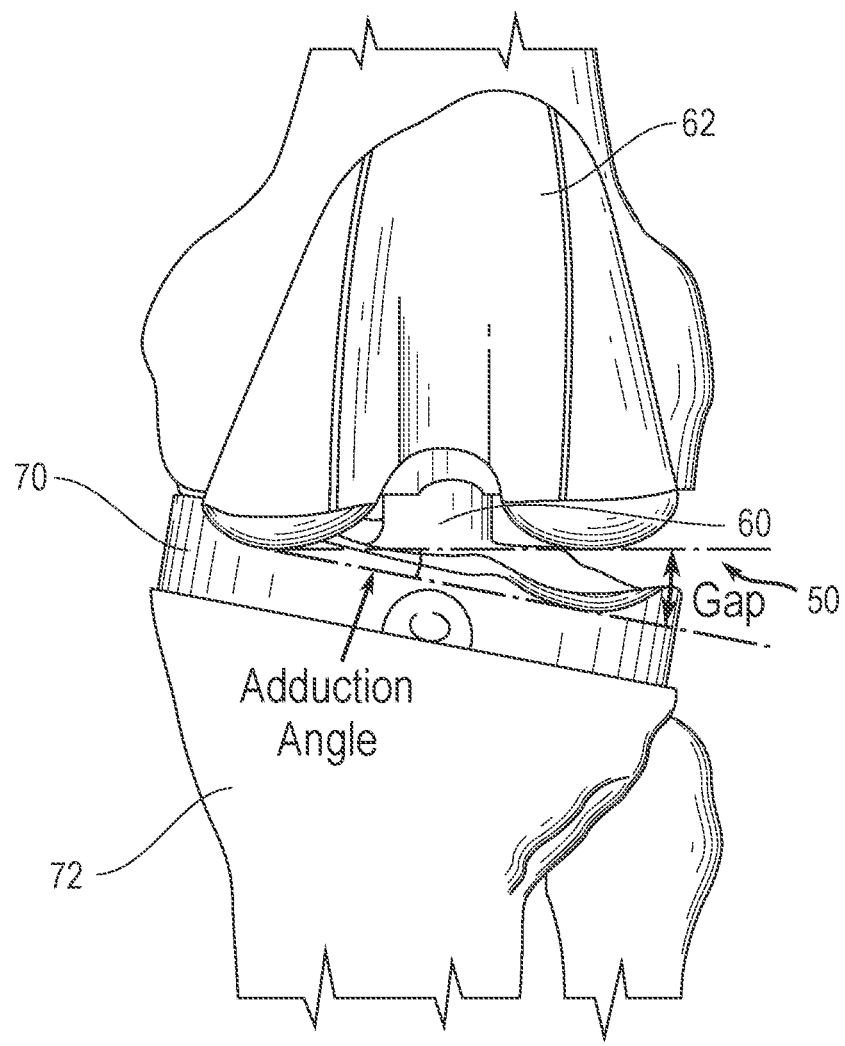
FIG. 2 illustrates an example three-dimensional ("3-D") model for demonstrating a calculation of a gap based on an adduction angle that was measured in accordance with an implementation of the present disclosure.

Referring now to FIG. 2, a three-dimensional ("3-D") model is shown for demonstrating a calculation of a gap based on an adduction angle that was measured in accordance with an implementation of the present disclosure. As shown in FIG. 2, a prosthetic implant 50 is provided with a femoral component 60 being attached to the femur bone 62, and a tibial component 70 being attached to the tibia bone 72. The gap between the femoral component 60 and the tibial component 70 is also shown. A similarly generated virtual 3-D model is further demonstrated in FIG. 7, which is generated using information received from sensors shown and described herein.

Figure 3A:
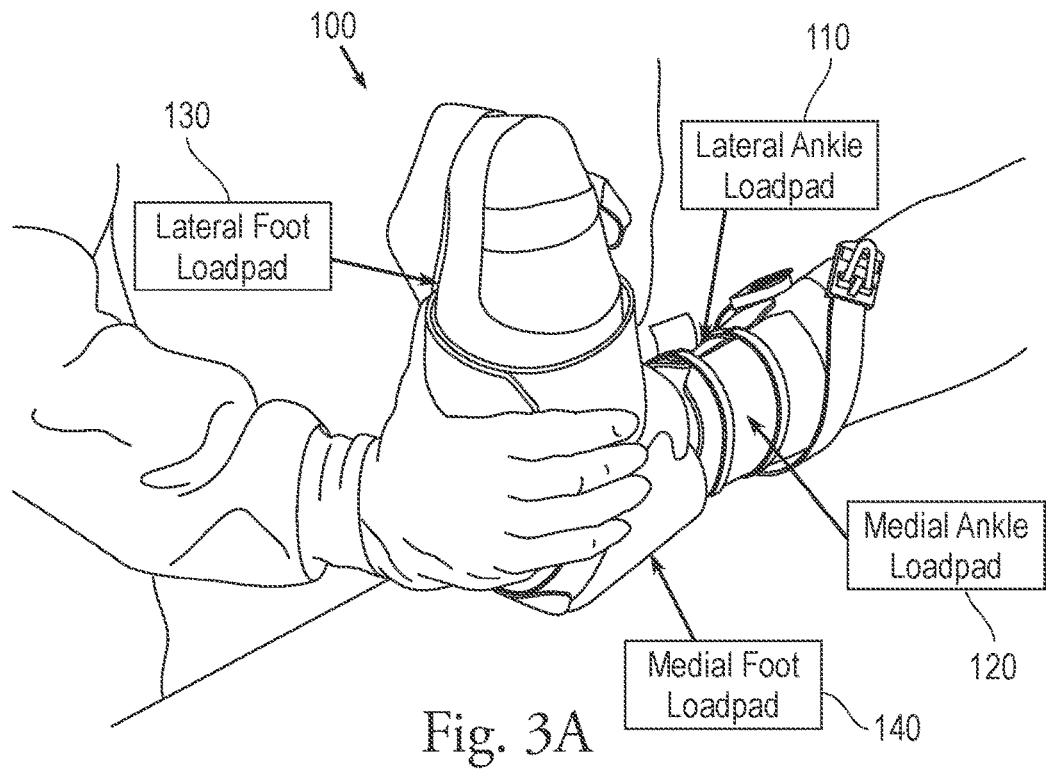
FIG. 3A illustrates a system which is used to measure forces that are applied as the surgeon performs abduction and adduction examinations, in accordance with an implementation of the present disclosure.

FIG. 3A illustrates the system (tool) 100 which is used to measure forces that are applied as the surgeon performs abduction-adduction examinations. In the example shown in FIG. 3A, system 100 is designed to be wrapped around the foot and the distal tibia of the patient. More specifically, the system 100 can include a wearable accessory that can have a main body, configured as a sleeve, that is placed over the lower leg and foot. The main body can be formed using various suitable fabrics or material that can be placed over the lower leg and foot. The main body can be secured to the leg and foot using a conventional securement mechanism. For example, the securement mechanism can be in the form of fasteners, such as hook and loop material, that allows a secure fit to be achieved.

In accordance with one or more implementations, the system 100 includes a plurality of sensors that are configured to detect applied forces and, in one or more exemplary implementations, at least four sensors are included, namely, a first sensor 110, a second sensor 120, a third sensor 130 and a fourth sensor 140. The first sensor 110 is a lateral ankle sensor for measuring applied forces at a lateral ankle position. The second sensor 120 is a medial ankle sensor for measuring applied forces at a medial ankle position. The third sensor 130 is a lateral foot sensor for measuring applied forces at a lateral foot position. The fourth sensor 140 is a medial foot sensor for measuring applied forces at a medial foot position. The sensors 110, 120, 130, 140 are designed to measure force that is applied at the location of the respective sensor.

It is also be appreciated that, in one or more implementations, the main body can be eliminated and that sensors 110, 120, 130, 140 can be individually secured to the leg and foot using conventional means such as fasteners (e.g., hook and loop material) or the like. For example, each sensor 110, 120, 130, 140 can be formatted as an elongated strip that can be wrapped around the leg and foot and secured thereto.

In one or more implementations, one or more of the sensors 110, 120, 130, 140 can comprise thin, flexible (pliable) sensors that are disposed along the body 110. One or more of the sensors 110, 120, 130, 140 can each comprise a force measurement sensor, or more such as commercially available from Novel Germany Any of the sensors 110, 120, 130, 140 can be configured as a pliable force sensor that is capable of being wrapped around a patient's foot and ankle for sensing applied force/torque and that provide quantified values representing the sensed force/torque. Moreover, values sensed by a respective sensor can be transmitted to one or more computing devices, e.g., via BLUETOOTH connectivity, thereby enabling calculation of the forces applied during the abduction and adduction examinations and automatic recommendations in connection with surgical methods and procedures, as well with respective implants to use.

In one or more implementations, the force sensor can be configured to measure a "normal" total force using a thin, flexible sensor to assess total force accurately, even if heterogeneously loaded across the sensor surface. For example, a LOADPAD® sensor has matchbox-sized electronics and communicates wirelessly via BLUETOOTH with a computing device, such as a smartphone, tablet, or other device. In one more implementations, a loadpad is a pliable, thin (4 mm thick), capacitive textile sensor that can measure the total loaded force even if the sensor surface was heterogeneously loaded. It is to be appreciated that other communication protocols can be used for communicating with a computing device. Values associated with various kinds of force can be displayed on a computing device (e.g., smartphone) substantially in real time. Further, user can also receive feedback regarding an applied force via an auditory, visual, or vibratory signal, substantially in real time. Moreover, measured data can be stored on the computing device (e.g., via memory) and/or to the cloud and/or transferred to another computer device (e.g., a desktop or laptop) for a more detailed analysis. Long-term measurements allow the evaluation of different parameters such as impulse, load frequency or loading rate.

In addition to hardware, one or more software applications can be provided to configure a computing device, such as a smartphone, to receive and process information received from force sensor(s), and to generate additional information in accordance with specific applications. For example, recommendations can be provided regarding implants, implant sizes, and amounts of force to use during gap assessment examination. Information can further be provided representing previous gap assessments, including to provide recommendations for one physician to provide consistent force.

In addition, the present disclosure supports various formatting of information for display, and various analysis of various parameters associated therewith. Data can also be exported for additional assessment, which may not be available within a respective software application operating on a given device. Thus, and in accordance with the present disclosure, use of force sensors provides accurate measurements and overcomes shortcomings associated with estimates to provide a complete assessment of the total force and/or torque, as well as for recommendations associated with procedural and insert options.

In one or more implementations the sensors are thin sensors, each having a thickness of about 4 millimeters. The four thin sensors can be placed between the surgeon's hand and the patient's leg/foot to measure forces applied by the surgeon. For example, two forces applied medially and two forces applied laterally are measured. The thin sensors are allowed to wrap around the foot and distal tibia to cover all the areas where the surgeon's hand touches the leg without interfering with the surgeon's techniques. In addition, medial and lateral placement of the thin sensors isolate push-pull forces applied during the abduction-adduction examination from the respective gripping forces. Further, a synthetic cast can be placed between the loadpad and the foot, which minimizes any bending of the loadpad due to gripping the foot.

As will be appreciated, the adduction and abduction stress tests are common in known attempts to reveal instability to medial or lateral displacement within the knee. For example, the adduction test involves placing the leg into extension, with one hand placed as a pivot on the knee. The abduction test involves applying forces to the knee in the opposite direction.

Figure 3B:
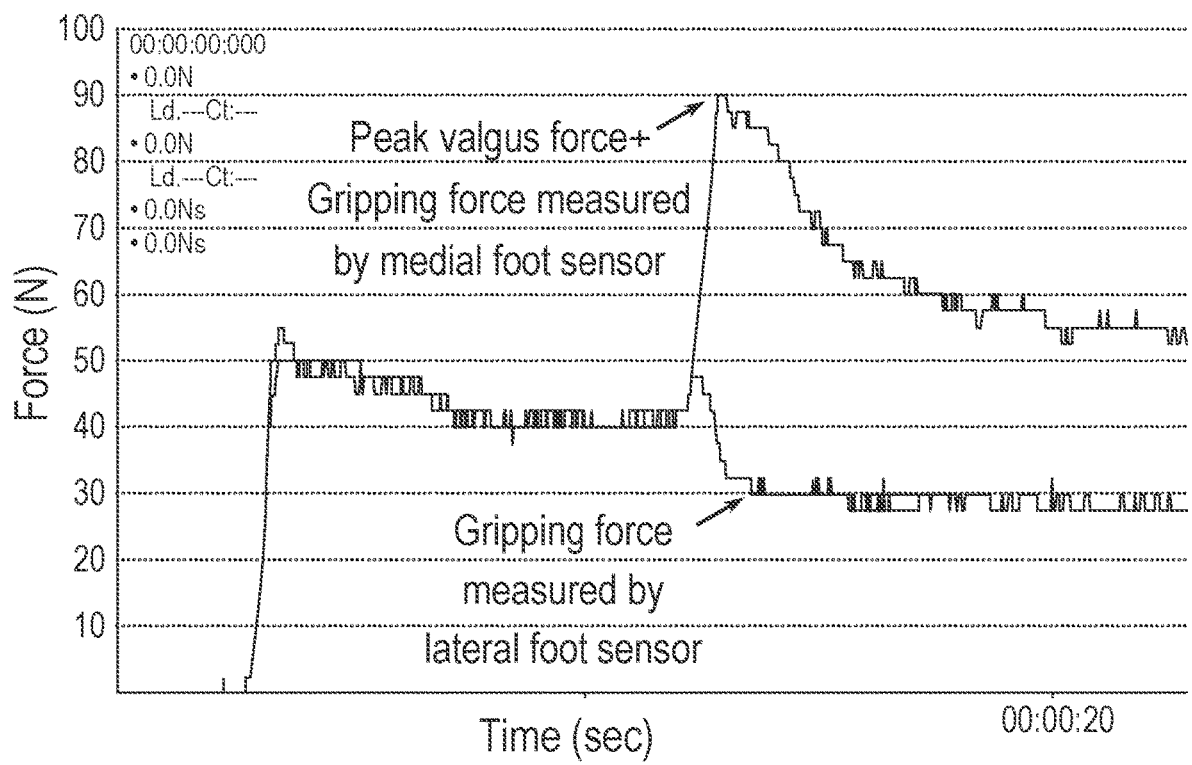
FIG. 3B shows a sample of data collected by force sensors, and demonstrates how gripping force is isolated from the push-pull force applied during the abduction-adduction examination in accordance with an implementation of the present disclosure.

FIG. 3B shows a sample of data collected by the force sensors 110, 120, 130, 140 and demonstrates how gripping force is isolated from the push-pull force applied during the abduction-adduction examination.

Figure 4:
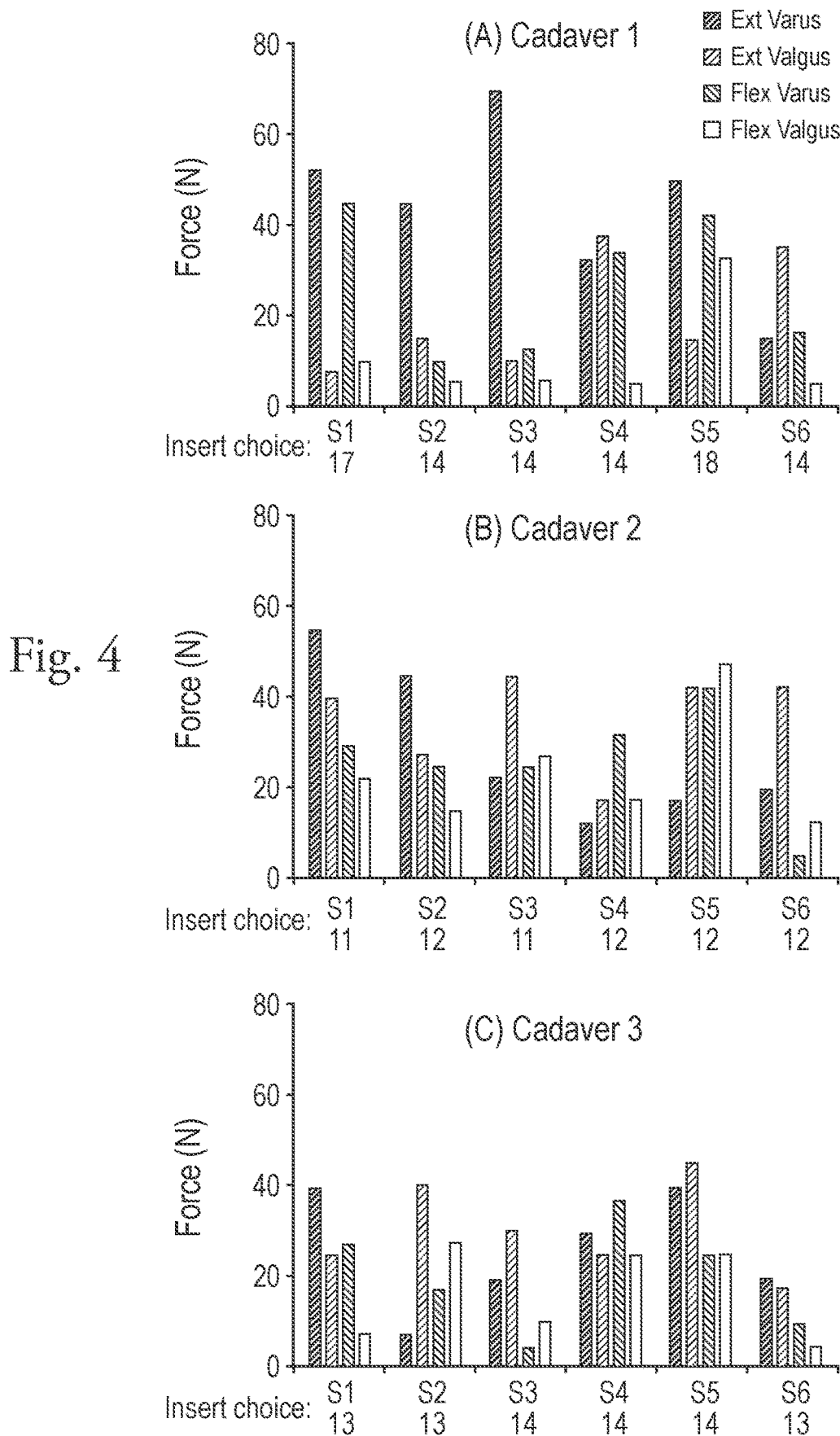
FIG. 4 includes bar graphs that indicate peak applied forces during an abduction-adduction examination in extension and flexion by six different surgeons, in accordance with an implementation of the present disclosure.

FIG. 4 includes bar graphs that indicate peak applied forces during an abduction-adduction examination in extension (Ext) and flexion (Flex) by six different surgeons (identified as S1 to S6). The forces are applied to three human bodies (identified in FIG. 4 as cadaver one (A), cadaver two (B), and cadaver three (C)). The choice of the insert size that was selected by each respective surgeon is reported under each surgeon, as noted as "Insert Choice:" in FIG. 4. In accordance with the example shown in FIG. 4, the six arthroplasty surgeons have varying levels of experience (from senior resident to >20 years in clinical practice). Each of the surgeons assessed ligament balance independently and selected the tibial insert that (s)he deemed to best fit each knee based on the surgeon's respective judgment. Surgeons could choose either a posterior stabilized ("PS") or a constrained posterior stabilized ("CPS") insert.

Continuing with the example in FIG. 4, once an insert was in place, each surgeon conducted the abduction-adduction examination in full extension and at 90° of flexion with their hands placed over the force sensors. Peak applied forces were measured and scaled by the distance between surgeon's hand and the knee joint line to obtain the applied torques. As noted above, four torques were measured: extension-abduction; extension-adduction; flexion-abduction; and flexion-adduction. The variation among surgeons in torque application was evaluated using repeated measures analysis of variance ("ANOVA"). The association between selected tibial insert thickness and peak applied torques can be evaluated using a generalized estimating equation (GEE) with a level of significance set at a threshold of 5% ($p<0.05$).

As set forth in the below Tables 1 and 2, below, the choice of the tibial insert thickness was found related to the magnitude of applied torques in abduction (Table 2): an incremental increase of 8 Nm of torque corresponded to the choice of a 1 mm thinner insert thickness.

TABLE 1

The choice of insert thickness of six surgeons (S1 to S6) for six cadavers (C1 to C7). CPS stands for mid-level constraint inserts. Surgeons arranged by seniority with S1 the most senior.

|  |  | Insert Thickness | | | | | | |
|---|---|---|---|---|---|---|---|---|
|  |  | C1 | C2 | C3 | C4 | C5 | C6 | C7 |
| Surgeons | S1 | 12 | 13 | 10 | 12 | 11 |  | 12 |
|  | S2 | 11 | 14 | 10 | $10_{(CPS)}$ | $10_{(CPS)}$ | 13 | 12 |
|  | S3 | 12 | 14 | 11 | 11 | 11 |  | 13 |
|  | S4 | 11 | 13 | 10 | 11 | 11 | 13 | 12 |
|  | S5 | 12 | $14_{(CPS)}$ | 10 | $12_{(CPS)}$ | $10_{(CPS)}$ | 14 | 13 |
|  | S6 | 12 | 13 | 10 | 12 | 10 |  | 12 |

TABLE 2

Regression analysis using generalized estimating equation
between the applied torques and the insert thickness choice.

| | Insert thickness | | |
|---|---|---|---|
| | Regression Coefficient (mm/Nm) | P-value | CI |
| Abduction extension | −0.06 | 0.027 | (−0.11, −0.01) |
| Adduction extension | −0.09 | 0.031 | (−0.18, −0.01) |
| Abduction 30° of flexion | −0.03 | 0.449 | (−0.11, 0.06) |
| Adduction 30° of flexion | −0.03 | 0.466 | (−0.11, 0.06) |
| Abduction 90° of flexion | −0.11 | 0.043 | (−0.22, 0.00) |
| Adduction 90° of flexion | 0.01 | 0.796 | (−0.06, 0.07) |

Generally, abduction-flexion torque differs more significantly among surgeons. Among the six surgeons, the choice of insert thickness varies by specimen by about 1 millimeter. Significant association was found between any of the applied torques at abduction extension, adduction extension, and abduction 90° of flexion and the surgeons' choices of insert thickness.

Figure 5:
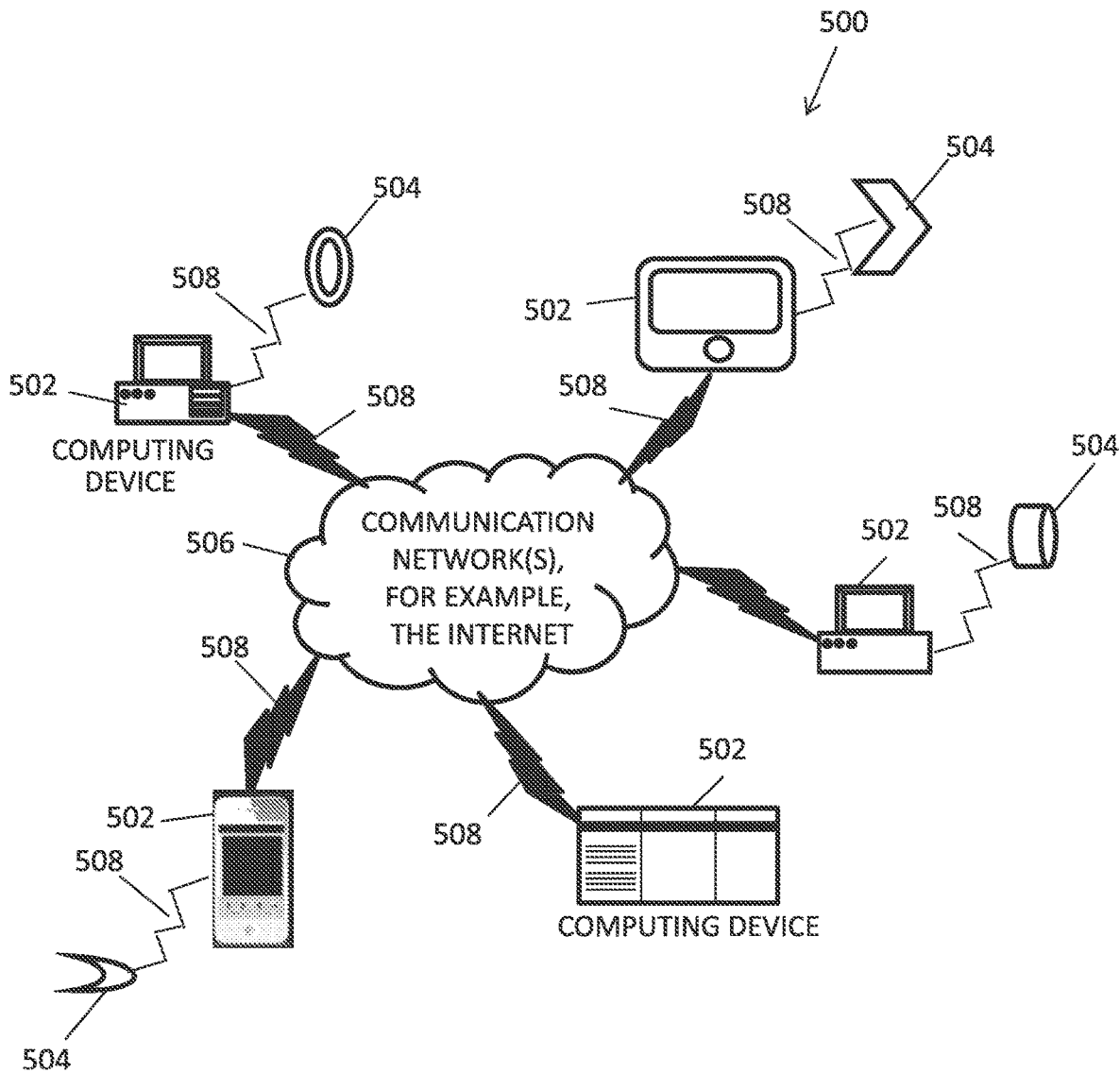
FIG. 5 shows an example hardware arrangement for obtaining, processing, and outputting information, in accordance with an example implementation.

FIG. 5 shows an example hardware arrangement 500 for obtaining, processing, and outputting information, including via a communication network 506, such as a local area network or a large-scale network (e.g., the Internet), in accordance with an example implementation. As shown in FIG. 5, one or more of a plurality of user computing devices, such as smartphones, tablet computers, laptop, or the like, are configured to receive data from one or more force sensors 504. Data can be communicated, for example, via transmissions 508. In the example illustrated in FIG. 5, force sensors 504 are pliable and are shown wrapped around a person's foot and ankle During use, force sensors 504 measure force (and, as a function of the application thereof), torque), such as applied by medical professionals preoperatively, intraoperatively by surgeons in an operating room, and/or postoperatively, and information associated with force/torque can be transmitted wirelessly to one or more computing device(s) 502 via a suitable data communications protocol, such as BLUETOOTH. In the example illustrated in FIG. 5, the present disclosure provides a decentralized system in which data acquisition, data storage, and data processing can occur as a function of independently operating and respectively configurable devices. The computing devices can be specially configured by executing software code to perform operations shown and described herein.

In one or more implementations, force information is received from force sensors 504 and processed by one or more computing devices 502 for various purposes, such as to determine an appropriate implant for a respective patient, as well as corresponding surgical procedures. For example, prior to or during a surgical procedure, a surgeon applies force, such as by holding a foot and applying abduction and adduction forces that generate abduction and adduction torques at or around the knee, and force sensors 504 operate to transmit force values. The values can be processed by one or more computing devices 502. For example, the computing device(s) 502 can calculate an adduction angle and/or to provide medial and lateral gaps, such as at different flexion and extension angles. In this way, the force sensors 504 and computing devices 502 operate to provide accurate gap assessment and can, thereafter, assist with surgical procedures, such as to determine an appropriate tibial insert size, whether to and how much to release ligaments or to modify the bone cuts to achieve proper soft tissue tension. Of course, one of ordinary skill will recognize that the arrangement in FIG. 5 is illustrative, and various combinations of one or more sensor(s) 504 and of one or more computing devices 502 can be applicable in accordance with the present disclosure.

Information associated with the present disclosure can be stored for various analyses and configurations. For example, a gap assessment examination is performed for a patient and information associated there with, such as information associated with force and/or torque during the gap assessment examination, is maintained in one or more databases. The information can be related to various kinds of information, such as by indexing or other known database management functionality, for further use. For example, information associated with gap assessment examinations is stored and related to a particular medical professional who performed the examination and a particular patient for whom the examination was performed. Thereafter, as another gap assessment examination is being performed, a correlation can be made by one or more computing devices 502 of the gap assessment examination with at least one previous gap assessment examination stored in a database. One or more correlations can be made associated with the same patient and the same medical professional, a different patient by the same medical professional, and at least one different patient and at least one different medical professional. Correlating information in this way allows for consistent examination procedure, which can improve accuracy of results even during gap assessment examinations, as well as patient care during examinations. For example, computing device 502 can alerts the medical professional by outputting an audible and/or visual alert during the examination that an amount of force or torque being applied is different than that of the same professional's previous exams, or different than other professionals' exams. Further, demographic information, such as the patient's age, gender, and physical size can be used by computing device 502 to alert the medical professional during a gap assessment examination that the amount of force and/or torque being applied by the medical professional is inconsistent with standards for the respective patient.

One or more sensors 504 can be configured to be suitably sized for respective applications, and configured with various components, such as capacitors, transducers, power supplies, memory, software (e.g., firmware), cables, and circuitry for sensing force and torque applied by a user (e.g., a physician or other medical personnel). In one or more implementations, a sensor 504 can include a communication module (e.g., communication subsystem) so that the sensor can communicate, either wired or wirelessly, the sensed data. Optionally, the sensor can directly or indirectly communicate sensed data to a microprocessor. As illustrated in FIG. 5, force sensors 504 can be configured in various shapes and sizes, as suitable for particular applications (e.g., for snug fitting on a patient). As shown and described herein, the use of force/sensors 504 provides a degree of reliability in the data reported because it eliminates user error and/or estimates.

The present disclosure supports computer-based systems and methods in connection with gap assessment and surgical procedure assistance, which include interactions between various hardware devices and information exchange via one or more user interfaces. These can be provided as a function of one or more computing devices 502 and sensors 504, and applications executing thereon. One or more computer-based applications can be implemented on various devices, such as via a microcontroller that includes a processor, a memory and code executing therein and/or a mobile computing device, such as a smartphone, so as to configure one or more processors to perform at least some of the functionality described herein. Computing device memory can store data and instructions suitable for controlling the operation of one or more processors. An implementation of memory can include, by way of example and not limitation, a random access memory (RAM), a hard drive, or a read only memory (ROM). One of the components stored in the memory is a program. Specific instances regarding collection and transmission of information, as well as validating, storing, and using such information in accordance with gap assessment and assistance with medical procedures are described in greater detail below.

Figure 6:
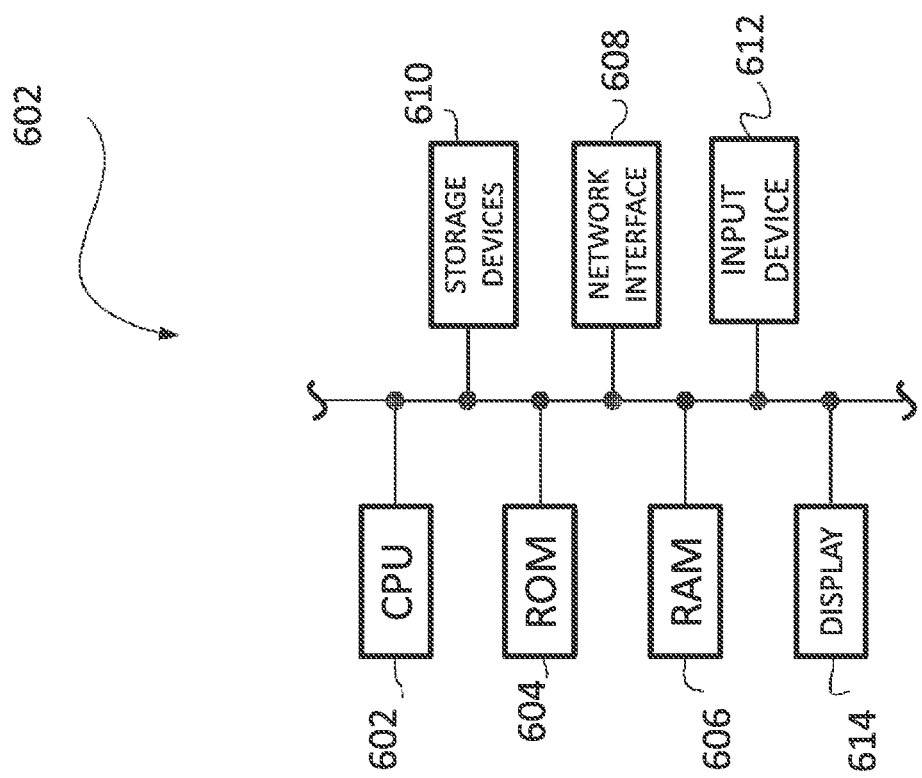
FIG. 6 illustrates one or more functional elements associated with a computing device and/or sensor, in accordance with an example implementation.

FIG. 6 illustrates one or more functional elements associated with a computing device 602 and/or sensor 604, and includes a processing subsystem having one or more central processing units (CPU) 602 used to execute software code and control the operation of device 602, and processor-readable media including, for example, read-only memory (ROM) 604, random access memory (RAM) 606, as well as one or more network interfaces 608 to transmit and receive data to and from other computing devices across a communication network, storage 610 such as a solid state memory, a hard disk drive, CD ROM or DVD ROM for storing program code, databases and application data, one or more input devices 612 such as a keyboard, mouse, track ball, virtual keyboard, touchscreen, microphone and the like, and a display 614. As noted herein, the force/sensor 604 can include a communication module (e.g., communication subsystem) so that the sensor can communicate, either wired or wirelessly, the sensed data.

Respective computer programs can include instructions that cause the processor 602 to execute steps that implement the methods described herein. The program can be implemented as a single module or as a plurality of modules that operate in cooperation with one another. The program can include software that can be used in connection with one or more implementations of the present disclosure. For example, a communication subsystem can be provided for communicating information from the microprocessor to a user interface, such as an external device (e.g., handheld unit or a computer that is connected over a network to the communication subsystem). Information can be communicated by the communication subsystem in a variety of ways including BLUETOOTH, Wi-Fi, Wi-Max, RF transmission, near-field communications or other suitable communication protocol. A number of different network topologies can be utilized in a conventional manner, such as wired, optical, 3G, 4G, 5G or other suitable networking protocol.

The communication subsystem can be part of a communicative electronic device including, by way of example, a smart phone or cellular telephone, a personal digital assistant (PDA), tablet computer, netbook, laptop computer, or other computing device. For instance, the communication subsystem can be directly connected through a device such as a smartphone such as an iPhone, Google Android Phone, Samsung Tizen, BlackBerry, and Microsoft Windows Mobile enabled phone, or a device such as a force and toque sensor or the like. One or more of these devices can include or otherwise interface with a module or communication unit with the subsystem to allow information and control signals to flow between the subsystem and an external user interface device. The communication sub-system can cooperate with a conventional communicative device, or can be part of a device that is dedicated to the purpose of communicating information processed by the microcontroller. Content provided in accordance with devices 602 can include, for example, numerical, textual, graphical, pictorial, audio and video material. Communication of such content can occur by and between one or more of the respective devices 602.

Figure 7:
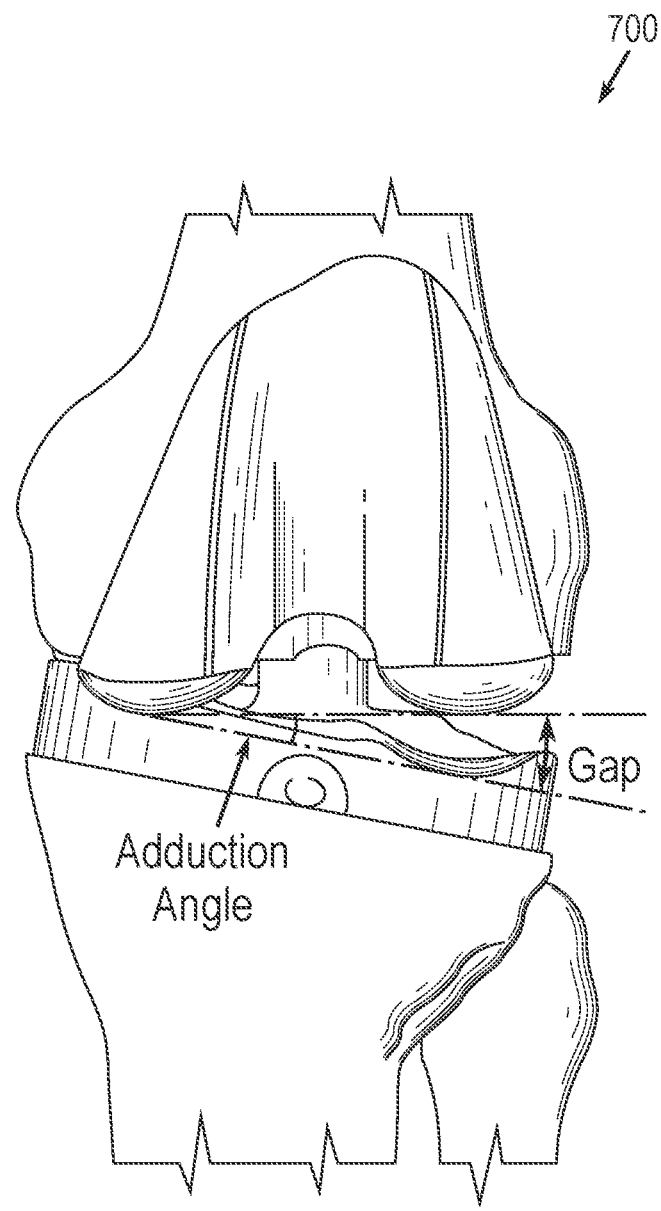
FIG. 7 illustrates and example 3-D model that demonstrates a calculation of a gap based on adduction angle that was measured using motion capture.

In one or more implementations, information received from sensor(s) 104 and processed by computing device(s) 602 can be used to define one or more sets of data points for representing gap assessment in a 3-D model. FIG. 7 illustrates and example 3-D model 700 that demonstrates a calculation of the gap based on adduction angle that was measured using motion capture. 3-D modeling, such as shown in FIG. 7, is particularly useful to identify respective gaps and to assist with determining a suitable implant, and to recommend whether to and how much to release ligaments or to modify the bone cuts to achieve proper soft tissue tension.

In addition to calculating a gap based on adduction angle and generating and/or displaying a 3-D model, an insert having a respective thickness can be determined and/or recommended for the surgeon. Moreover, determinations can be made to identify whether force, including at particular angles, are applied consistently across different times for a single surgeon or across several surgeons. For example, the present disclosure supports ensures that consistent force is applied by a medical professional prior to, during, and/or after surgery, which improves the accuracy of gap assessment and the result of surgical procedures over time.

Further, in one or more implementations a threshold value of force can be detected within a respective range for a different kind of force (e.g., axial or linear). In one or more implementations, baseline information can be obtained as a function of a patient's age, gender, weight, or other measurements and used to determine a respective range of acceptable force for the particular patient. One or more outputs, such as an audible output or output on a display, can be provided to the surgeon, including during surgery or preparation therefor, to alerts the surgeon that a particular amount of force is within or outside of the respective range.

Thus, in accordance with the teachings herein, recommendations associated with an implant size, amount of force, and angle of force can be provided preoperatively, during an operation, and postoperatively.

Figure 8:
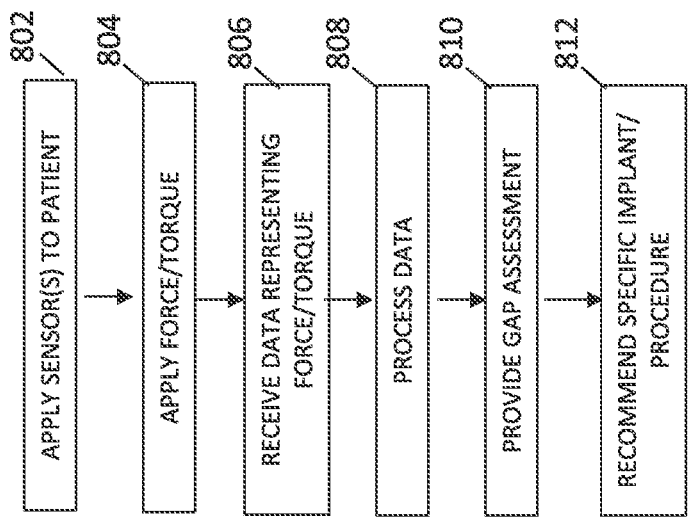
FIG. 8 is a flowchart illustrating steps associated with an example implementation of the present disclosure.

FIG. 8 is a simple flowchart illustrating steps associated with an example implementation of the present disclosure. At step 802, sensor(s) are applied to a patient. At step 804, force/torque is applied and, thereafter, data representing the force as sensed by the sensors are received. Thereafter, at step 806, the data are processed (step 808) and a gap assessment is provided (810). Using the gap assessment and various processing associated with the respective medical procedure, a specific implant (e.g., a tibial implant) is recommended as is a respective procedure, such as whether to and how much to release ligaments or to modify the bone cuts to achieve proper soft tissue tension (step 812).

Three cadaveric knees (A, B, C) were implanted with standard TKA trial implants. The four pliable sensors 110, 120, 130, 140 were wrapped around the foot and ankle of each cadaver to measure the push-pull forces applied during the abduction-adduction examination. Six surgeons (S1-S6) with varying experience independently conducted an abduction-adduction examination in extension and flexion and reported the gaps that they observed. Motion capture was used to measure the gaps between femur and tibia by placing cluster of reflective markers on the femur and tibia as shown in the figures. Subsequently, each surgeon chose the tibial insert that they thought best fit for each knee. The measured peak applied forces were related to the insert thickness and the measured gaps were compared to the observed gaps by surgeons. Since insert thickness was in 1 mm increments, 1 mm gap error was considered a meaningful difference.

The peak forces varied among surgeons for each cadaver. In cadaver one (A)m the peak forces in abduction and adduction in extension were 48±20 and 20±12 N and in flexion, they were 27±14 and 8±11 N. Peak forces in cadavers two (B) and three (C) were similar, in abduction and adduction, in extension 24±14 and 35±10 N, and in flexion, 23±12 and 20±10 N, respectively. It was observed that the larger the adduction force in extension, the insert choice was thinner ($\beta=-0.09$ mm/N, p=0.031).

In extension, the difference between estimated gaps and measured gaps was >1 mm for 36% of all assessments and 91% of all gaps were underestimated. Only one measure, however, was underestimated by >2 mm. In flexion, gap estimates were >1 mm for 35% of all measurements and 59% of all measurements were overestimated. Four measures were overestimated, and one was underestimated by >2 mm.

In seven non-arthritic cadaveric knees installed with primary TKA, we found that the applied abduction and adduction torques during gap balance examination varied among six surgeons independent of their level of experience, but the variation was significant in only abduction-flexion torque (P<0.001). The choice of tibial insert thickness for each cadaver trial varied by only 1 mm across all surgeons and was related to the magnitude of the applied torques (P<0.05) in adduction extension, abduction extension, and abduction 90° of flexion. This suggests that although applied torques may vary across surgeons during the intraoperative examination, the surgeons are likely to arrive at similar decisions of the most appropriate insert thickness.

Applicant discovered that the applied forces varied among surgeons and a negative association between insert thickness and forces in extension adduction, extension abduction, and 90° of flexion abduction examinations. Applicant also discovered that error in gap estimates among surgeons was >1 mm a third of the time and that underestimation is more common in full extension which can lead to using smaller inserts that affect knee stability.

The present system and method provide a means to quantify the applied forces/torques during the intraoperative gap assessment exams and understand the relationship between these forces/torques and subsequent surgical decisions. This system and method provide for a valuable teaching aid as discussed herein for the training of residents and fellows.

Thus, as shown and described herein the present disclosure provides several advantages in connection with physical examination, including gap assessment examinations. Such improvements and advantages include, but are not limited to, the following. Force and torque measurements during gap assessment examinations can be quantified and information associated therewith can be provided substantially in real-time during the examination. Further, forces can be measured intraoperatively, which allow for improved control and guidance as to how a respective gap assessment examination is being performed. This provides an additional benefit of standardizing the examination process. Moreover, the application of force sensors can be integrated with other kinds of navigation technology or intraarticular sensors, and supports providing live feedback to surgeons, which can help guide or influence subsequent decisions during a procedure. Moreover, use of force sensors in accordance with the present disclosure is particularly useful to provide a teaching tool for medical professionals, such as residents, fellows, and junior attendants, and can enhance professionals' intuition and knowledge for performing gap assessment examinations.

While this disclosure contains many specific implementation details, these should not be construed as limitations on the scope of any implementation or of what can be claimed, but rather as descriptions of features that can be specific to particular embodiments of particular implementations. Certain features that are described in this disclosure in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

Further, while many of the examples and discussion herein regards gap assessment examinations and improvements thereto, the present disclosure is not so limited. For example, the teachings herein can generally be used as a quantitative objective assessment tool for any virtually condition (e.g., an injury) or procedure requiring physical examination of a patient's joint. Moreover, the present disclosure is usable for many physical examinations and/or procedures, and is not intended to be limited to arthroplasty. For example, sports knee examinations, and examinations of the foot, ankle, spine, and shoulder are applicable in accordance with the teachings herein. Further, and as noted herein, such examinations can be used preoperatively, intraoperatively, and postoperatively as part of the physical examination of the patient.

Moreover, the configuration of force sensors allows for isolation of push and pull forces, including from the squeezing force provided by a surgeon. This could be used to measure forces associated with a twist, a push, a pull, or a combination thereof and in any direction. Generally, the configuration could be used to assess translations, rotations or combinations thereof in response to quantitative pushes, pulls, and/or twists be integrated with inertial sensors—also shown in FIG. 1 (e.g., positioned closer to the knee), motion capture is less practical for patient applications outside the operating room. The set-up could be used not only to make intraoperative decisions, such as bone cut or insert size, but also for preoperative and postoperative assessments, including the degree of contracture or the level of tissue injury and damage or the degree of tissue stretching over time. Furthermore, the force sensors can be configured about other joints, to provide similar assessments as described here, such as in connection with the cervical spine, the hindfoot, or the like.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this disclosure, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this disclosure have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing can be advantageous.

What is claimed is:

1. A system for assessing measured forces that are applied by a medical professional during a gap assessment examination associated with an arthroplasty procedure for a patient, the system comprising:
    a plurality of force sensors, each one of the plurality of force sensors respectively placed at i) a lateral ankle position and a medial ankle position, ii) a lateral foot position and a medial foot position, or iii) a lateral ankle position and a medial ankle position and a lateral foot position and a medial foot position, and each of the plurality of force sensors configured to detect an applied force at i) the lateral ankle position and the medial ankle position, ii) the lateral foot position and the medial foot position, or iii) the lateral ankle position and the medial ankle position and the lateral foot position and the medial foot position, respectively, during an abduction-adduction examination;
    a computing device having at least one processor, a memory, and an output, and that is configured by executing instructions to:
        receive, from each of the plurality of sensors during the abduction-adduction examination, data representing an applied force occurring during the abduction-adduction examination at each respective ones of i) the lateral ankle position and the medial ankle position, ii) the lateral foot position and the medial foot position, or iii) the lateral ankle position and the medial ankle position and the lateral foot position and the medial foot position;
        calculate, using the received data, respective peak applied forces during the abduction-adduction examination in extension and flexion;
        provide, via the output, information representing a correlation of the respective peak applied forces with information associated with at least one of:
            at least one previous gap assessment examination for the patient by the medical professional;
            at least one previous gap assessment examination for a different patient by the medical professional; and
            at least one previous gap assessment examination for at least one different patient by at least one different medical professional.

2. The system of claim 1, wherein the computing device is further configured by executing instructions to:
    determine medial and lateral gaps at different flexion and extension angles during the gap assessment examination.

3. The system of claim 2, wherein the information representing the correlation is in accordance with the determined medial and lateral gaps, and further wherein the information representing the correlation includes at least one of an accurate gap assessment examination and information associated with at least one surgical procedure.

4. The system of claim 3, wherein the information associated with at least one surgical procedure includes a recommended insert size, a recommendation for a bone cut to achieve a threshold of soft tissue tension, or a degree to release ligaments.

5. The system of claim 1, wherein the computing device is further configured by executing instructions to:
    track, as a function of at least one marker, bone or joint movement during the gap assessment examination; and
    measure, as a function of the movement, an abduction-adduction angle or degree of rotation.

6. The system of claim 1, wherein the computing device is further configured by executing instructions to: generate and provide, via the output, a 3-D model that demonstrates a gap based on a measured abduction-adduction angle.

7. The system of claim 1, wherein the output comprises a display, and further wherein the information representing the correlation is formatted as a graph.

8. The system of claim 1, wherein each of the plurality of sensors comprises an elongated sensor that is configured to measure a total force, and further comprises internal electronics and a communications module to permit wireless transmission of data to a remote computing device.

9. The system of claim 1, wherein the computing device is further configured by executing instructions to:
    record applied force measurements, from each of the plurality of sensors, during an abduction examination in flexion;
    record applied force measurements, from each of the plurality of sensors, during an abduction examination in extension;
    record applied force measurements, from each of the plurality of sensors, during an adduction examination in flexion; and
    record applied force measurements, from each of the plurality of sensors, during an adduction examination in extension;
    wherein the information representing the correlation is in accordance with each of the recorded applied force measurements.

10. A method for assessing measured forces that are applied by a medical professional during a gap assessment examination associated with an arthroplasty procedure for a patient, the method comprising:

positioning a plurality of force sensors respectively at i) a lateral ankle position and a medial ankle position, ii) a lateral foot position and a medial foot position, or iii) a lateral ankle position and a medial ankle position and a lateral foot position and a medial foot position, wherein each of the plurality of force sensors is configured to detect an applied force at i) the lateral ankle position and the medial ankle position, ii) the lateral foot position and the medial foot position, or iii) the lateral ankle position and the medial ankle position and the lateral foot position and the medial foot position, respectively, during an abduction-adduction examination;

receiving, by a computing device having at least one processor, a memory, an output, and that is configured by executing instructions, from each of the plurality of sensors during the abduction-adduction examination, data representing an applied force occurring during the abduction-adduction examination at each respective ones of i) the lateral ankle position and the medial ankle position, ii) the lateral foot position and the medial foot position, or iii) the lateral ankle position and the medial ankle position and the lateral foot position and the medial foot position;

calculating, by the computing device using the received data, respective peak applied forces during the abduction-adduction examination in extension and flexion;

providing, by the computing device via the output, information representing a correlation of the respective peak applied forces with information associated with at least one of:
  at least one previous gap assessment examination for the patient by the medical professional;
  at least one previous gap assessment examination for a different patient by the medical professional; and
  at least one previous gap assessment examination for at least one different patient by at least one different medical professional.

11. The method of claim 10, further comprising:
determining, by the computing device, medial and lateral gaps at different flexion and extension angles during the gap assessment examination.

12. The method of claim 11, wherein the information representing the correlation is in accordance with the determined medial and lateral gaps, and further wherein the information representing the correlation includes at least one of an accurate gap assessment examination and information associated with at least one surgical procedure.

13. The method of claim 12, wherein the information associated with at least one surgical procedure includes a recommended insert size, a recommendation for a bone cut to achieve a threshold of soft tissue tension, or a degree to release ligaments.

14. The method of claim 10, further comprising:
tracking, by the computing device as a function of at least one marker, bone or joint movement during the gap assessment examination; and
measuring, by the computing device as a function of the movement, an abduction-adduction angle or degree of rotation.

15. The method of claim 10, further comprising: generating and providing, by the computing device via the output, a 3-D model that demonstrates a gap based on a measured abduction-adduction angle.

16. The method of claim 10, wherein the output comprises a display, and further wherein the information representing the correlation is formatted as a graph.

17. The method of claim 10, wherein each of the plurality of sensors comprises an elongated sensor that is configured to measure a total force, and further comprises internal electronics and a communications module to permit wireless transmission of data to a remote computing device.

18. The method of claim 10, further comprising:
recording, by the computing device, applied force measurements, from each of the plurality of sensors, during an abduction examination in flexion;
recording, by the computing device, applied force measurements, from each of the plurality of sensors, during an abduction examination in extension;
recording, by the computing device, applied force measurements, from each of the plurality of sensors, during an adduction examination in flexion; and
recording, by the computing device, applied force measurements, from each of the plurality of sensors, during an adduction examination in extension;
wherein the information representing the correlation is in accordance with each of the recorded applied force measurements.

19. A system for assessing measured forces that are applied by a medical professional during a physical examination of a patient, the system comprising:
a plurality of force sensors, each one of the plurality of force sensors respectively placed at positions at or about joints of the patient, and each of the plurality of force sensors configured to detect, during the physical examination, an applied force at each force sensor's respective position;
a computing device having at least one processor, a memory, and an output, and that is configured by executing instructions to:
  receive, from each of the plurality of sensors during the physical examination, data representing an applied force occurring during the physical examination at each respective ones of the positions;
  calculate, using the received data, respective peak applied forces during the physical examination;
  provide, via the output, information representing a correlation of the respective peak applied forces with information associated with at least one of:
    at least one previous physical examination for the patient by the medical professional;
    at least one previous physical examination for a different patient by the medical professional; and
  at least one previous physical examination for at least one different patient by at least one different medical professional.

* * * * *